(12) United States Patent
Chang

(10) Patent No.: US 6,394,100 B1
(45) Date of Patent: May 28, 2002

(54) REUSABLE ARTIFICIAL FINGERNAIL HAVING MOLDED TEXTURED SURFACE

(75) Inventor: Sung Yong Chang, Roslyn Heights, NY (US)

(73) Assignee: KMC Exim Corp., Port Washington, NY (US)

( * ) Notice: Subject to any disclaimer, the term of this patent is extended or adjusted under 35 U.S.C. 154(b) by 0 days.

(21) Appl. No.: 09/643,465

(22) Filed: Aug. 22, 2000

(30) Foreign Application Priority Data

May 1, 2000 (KR) .............................. 00-23249

(51) Int. Cl.$^7$ .............................................. A45D 31/00
(52) U.S. Cl. ........................ 132/200; 132/73; 264/222; 264/DIG. 30
(58) Field of Search ........................ 132/73, 73.5, 200, 132/285

(56) References Cited

U.S. PATENT DOCUMENTS

| | | | |
|---|---|---|---|
| 1,942,332 A | | 1/1934 | Hamberg |
| 2,607,356 A | * | 8/1952 | Lewis .......................... 132/73 |
| 2,633,139 A | | 3/1953 | Pettey |
| 2,746,460 A | | 5/1956 | Jellinek |
| 2,764,166 A | | 9/1956 | Bogoslowsky |
| 2,864,384 A | | 12/1958 | Walter |
| 2,979,061 A | | 4/1961 | Greenman et al. |
| 3,008,850 A | | 11/1961 | Ulrich |
| 3,502,088 A | | 3/1970 | Jarby |
| 3,898,357 A | | 8/1975 | Miller et al. |
| 3,924,044 A | | 12/1975 | Gobran et al. |
| 4,151,319 A | | 4/1979 | Sackoff et al. |
| 4,273,145 A | | 6/1981 | Lester et al. |
| 4,511,608 A | | 4/1985 | Ferraro |
| 4,536,426 A | | 8/1985 | Massey |
| 4,745,934 A | | 5/1988 | Mast et al. |
| 4,824,702 A | | 4/1989 | Straub |
| 4,860,774 A | | 8/1989 | Becker |
| 4,876,121 A | | 10/1989 | Cohen |
| 4,903,840 A | | 2/1990 | So |
| 4,920,991 A | | 5/1990 | Shibahashi et al. |
| 4,947,876 A | | 8/1990 | Larsen |
| 5,044,384 A | | 9/1991 | Hokama et al. |
| 5,219,645 A | | 6/1993 | Schoon |
| 5,294,657 A | * | 3/1994 | Melendy et al. ............. 524/270 |
| 5,413,123 A | | 5/1995 | Aylott et al. |
| 5,415,903 A | | 5/1995 | Hoffman et al. |
| 5,699,813 A | * | 12/1997 | Carroll .......................... 132/73 |
| 5,824,180 A | * | 10/1998 | Mikuni et al. ............ 156/275.3 |
| 5,860,429 A | * | 1/1999 | Chang .......................... 132/73 |
| 5,968,302 A | * | 10/1999 | Gifford ......................... 156/245 |
| 5,977,205 A | * | 11/1999 | Messere et al. .............. 523/113 |
| 6,042,679 A | | 3/2000 | Holt et al. |

FOREIGN PATENT DOCUMENTS

| | | | |
|---|---|---|---|
| EP | 0010758 A1 | * 10/1979 | ........... C08G/18/10 |
| EP | 0 010 758 | 5/1980 | |
| GB | 709286 | 5/1954 | |
| JP | 10-146214 | 6/1998 | |

\* cited by examiner

Primary Examiner—Todd E. Manahan
Assistant Examiner—David C. Comstock
(74) Attorney, Agent, or Firm—Hoffmann & Baron, LLP

(57) ABSTRACT

An ornamental accessory for a fingernail comprises an overlay having a reusable pressure-sensitive adhesive layer pre-applied to a bottom surface thereof for application and bonding to the wearer's natural nail, and a method of making the same. The adhesive formulation is a copolymer of acrylic ester and vinyl acetate formed from an aqueous acrylic copolymer emulsion. The bottom surface of the overlay to which the adhesive is applied is textured to enhance adhesion of the adhesive layer. A method for forming a pre-glued ornamental fingernail accessory includes the steps of forming an overlay having the shape and size of a natural fingernail and applying an aqueous copolymer emulsion, as described above, to a bottom surface of the overlay. The emulsion is allowed to cure whereby a substantial portion of the water in the emulsion is evaporated to form a reusable pressure-sensitive adhesive layer fixed to the overlay. The pressure-sensitive adhesive layer is reactivated by adding an aqueous solution to the dried aqueous copolymer emulsion.

22 Claims, 2 Drawing Sheets

REUSABLE ARTIFICIAL FINGERNAIL HAVING MOLDED TEXTURED SURFACE

BACKGROUND OF THE INVENTION

The present invention relates to the art of ornamental accessories for fingernails, and, in particular, to an artificial fingernail having a pre-applied adhesive layer fixed thereto.

It has been known in the art of adorning the hands to provide ornamental fingernail accessories made from thin, molded plastic members manufactured generally in the shape of a fingernail. Typically, the wearer must apply an amount of a liquid bonding adhesive to the accessory and/or the natural nail and affix the accessory to the nail. Usually the wearer must wipe or trim away any excess adhesive and then wait several moments until the adhesive dries to ensure that the accessory is secured to the nail. When it is desired to remove the accessory, the wearer typically must soak the fingernail with the attached accessory in a solvent for a sufficient amount of time to dissolve the adhesive. Such process is difficult, time consuming and damaging to the natural fingernail.

An alternative to this process is set forth in U.S. Pat. No. 4,745,934 to Mast et al. which discloses an adhesive press-on tab system for attaching artificial fingernails to the wearer's natural nails. The tabs are essentially double-sided adhesive tape with removable liners that are interposed between the artificial fingernail and the natural fingernail. However, applying the tabs and fingernail accessories is still time consuming and cumbersome. Additionally, the stacking of the tab and accessory results in a nail that does not look natural and is prone to being dislodged.

Attempts have been made to provide an ornamental fingernail accessory having a pre-applied pressure sensitive adhesive layer with varying degrees of success. For example, U.S. Pat. No. 5,415,903 to Hoffman et al. discloses a self adhesive laminate having an adhesive composition made of an acrylate copolymer requiring acrylic acid and titanium chelate ester. U.S. Pat. No. 6,042,679 to Holt et al. discloses that an acrylic pressure sensitive adhesive known in the art can be used in a method for treating damaged fingernails. U.S. Pat. No. 5,044,384 to Hokama et al. discloses that a pressure-sensitive adhesive known in the art can be used in a method for accomplishing a rapid and durable manicure. U.S. Pat. No. 4,860,774 to Becker discloses that a commercially available pressure-sensitive adhesive can be used in a method for fingernail reinforcement. In addition, several other patents generally disclose pre-applying an adhesive to an artificial fingernail.

Some of the problems associated with the artificial fingernails of the prior art include weak adhesive strength, damage to the natural nail, short adhesive shelf-life, non-reusable adhesives, a cosmetically unappealing appearance and time-consuming or difficult application. Accordingly, it would be desirable to provide an ornamental fingernail accessory that solves these shortcomings of the prior art in a commercially efficient manner.

SUMMARY OF THE INVENTION

The present invention is an ornamental accessory for a fingernail comprising an overlay having a reusable pressure-sensitive adhesive layer pre-applied to a bottom surface thereof for application and bonding to the wearer's natural nail, and a method of making the same.

The adhesive formulation is a copolymer of acrylic ester and vinyl acetate. The pre-applied adhesive is formed from an aqueous acrylic copolymer emulsion comprising about 35% water and 65% copolymer. Preferably, the bottom surface of the overlay to which the adhesive is applied is textured to enhance adhesion of the adhesive layer. The adhesive layer exhibits superior peel strength and is easily applied to the overlay. The adhesive layer may also include glitter or may be colored for decorative purposes. The overlay is made from a mixture of ABS plastic and a polycarbonate and may take the form of a fingernail cover or a fingernail tip.

In a method for forming a pre-glued ornamental fingernail accessory, an overlay having the shape and size of a natural fingernail is formed and an aqueous copolymer emulsion, as described above, is applied to a bottom surface of the overlay. The emulsion is allowed to cure whereby a substantial portion of the water in the emulsion is evaporated to form a reusable pressure-sensitive adhesive layer fixed to the overlay. The pressure-sensitive adhesive layer is reactivated by adding an aqueous solution to the cured aqueous copolymer emulsion.

As a result of the present invention, an artificial nail having a pre-applied adhesive layer is provided which is easily attached to the natural fingernail. The significantly improved adhesive layer is reusable so that the wearer can easily remove and reattach the artificial nail as desired without damaging or leaving adhesive on the natural nail.

For better understanding of the present invention, reference is made to the following description, taken in conjunction with the accompanying drawings, and its scope will be pointed out in the appended claims.

DETAILED DESCRIPTION OF THE PREFERRED EMBODIMENTS

Figure 1:
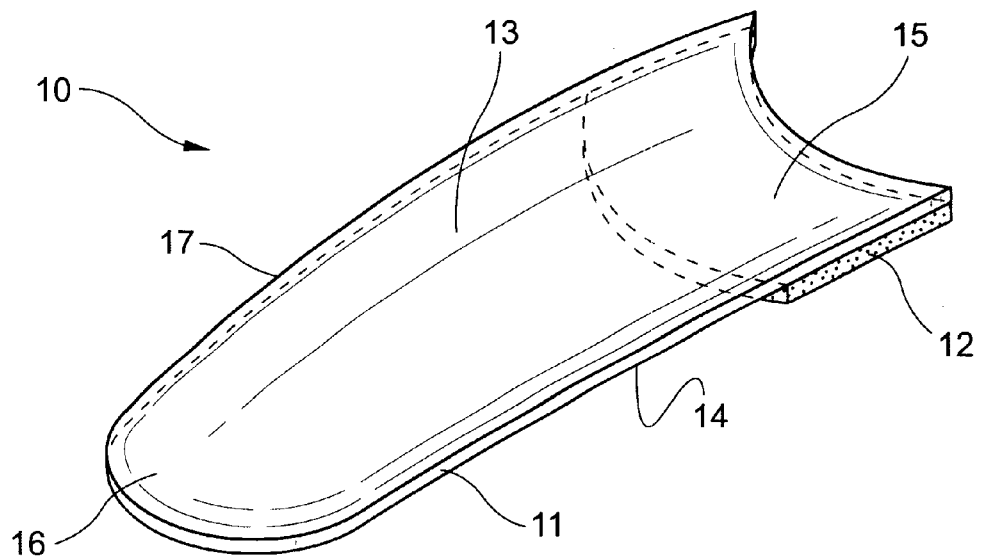
FIG. 1 is a top perspective view of the pre-glued ornamental fingernail accessory in the form of a fingernail tip formed in accordance with the present invention.

Referring to the drawings, the preferred embodiments of a pre-glued ornamental fingernail accessory of the present invention are shown. The accessory 10 generally includes an elongated overlay 11, and a pressure-sensitive adhesive layer 12 fixed to a bottom surface of the overlay.

Figure 2:
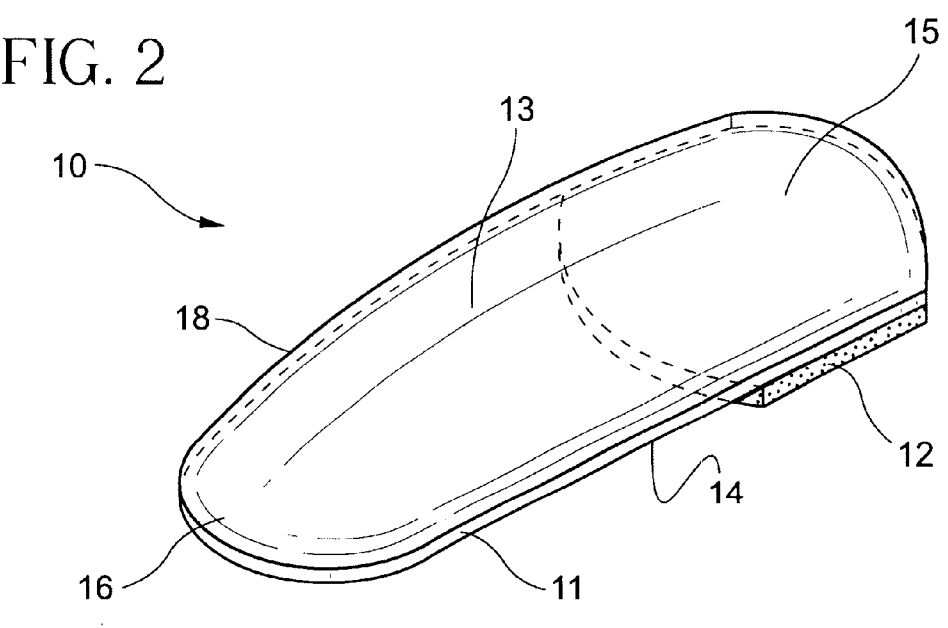
FIG. 2 is a top perspective view of the pre-glued ornamental fingernail accessory in the form of a fingernail cover formed in accordance with the present invention.

The overlay 11, has a top surface 13, a bottom surface 14, a first end (or proximal end) 15, and a second end (or distal end) 16. The first end 15 should be in the shape and size approximating the shape and size of at least the end of a fingernail of a wearer. In the case of a fingernail tip 17, as shown in FIG. 1, the first end 15 is in the shape and size approximating the shape and size of the end of a fingernail of a wearer. In the case of a fingernail cover 18, as shown in FIG. 2, the first end 15 is in approximately the shape and size of a full natural fingernail.

The overlay 11 is generally of uniform thickness but may decrease in thickness (i.e. taper) at the first end to facilitate attachment and blending with the natural fingernail. The overlay 11 is preferably made from a plastic like material commonly employed in the manufacture of artificial nails, (i.e., ABS plastic, nylon, tenite acetate, vinyl acetate, polycarbonates, etc.) using conventional injection molding techniques known in the art. In a preferred embodiment, the overlay 11 is made from a mixture of ABS plastic and a polycarbonate, with a greater amount of ABS plastic than the polycarbonate. The overlay 11 may be transparent, translucent or opaque. In a preferred embodiment, the overlay 11 is transparent so that decorative additives included in the adhesive layer 12 may be visible through the overlay.

Figure 3:
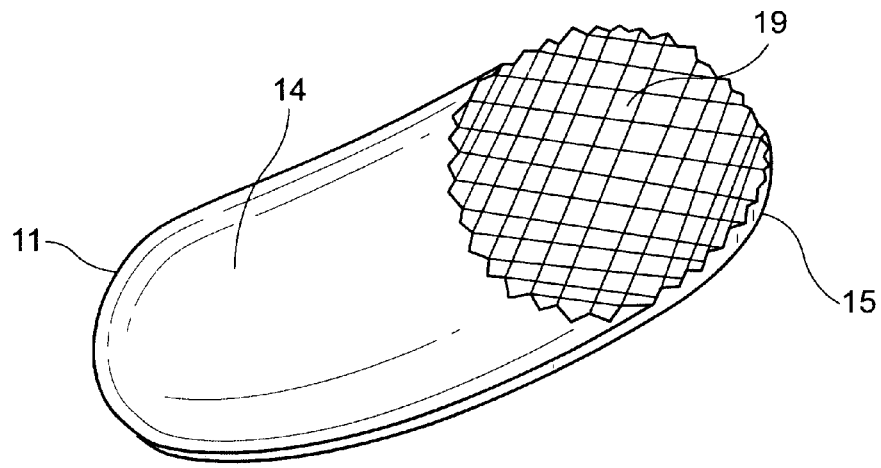
FIG. 3 is a bottom perspective view of the overlay of the present invention in the form of a fingernail cover showing the textured bottom surface.
Figure 4:
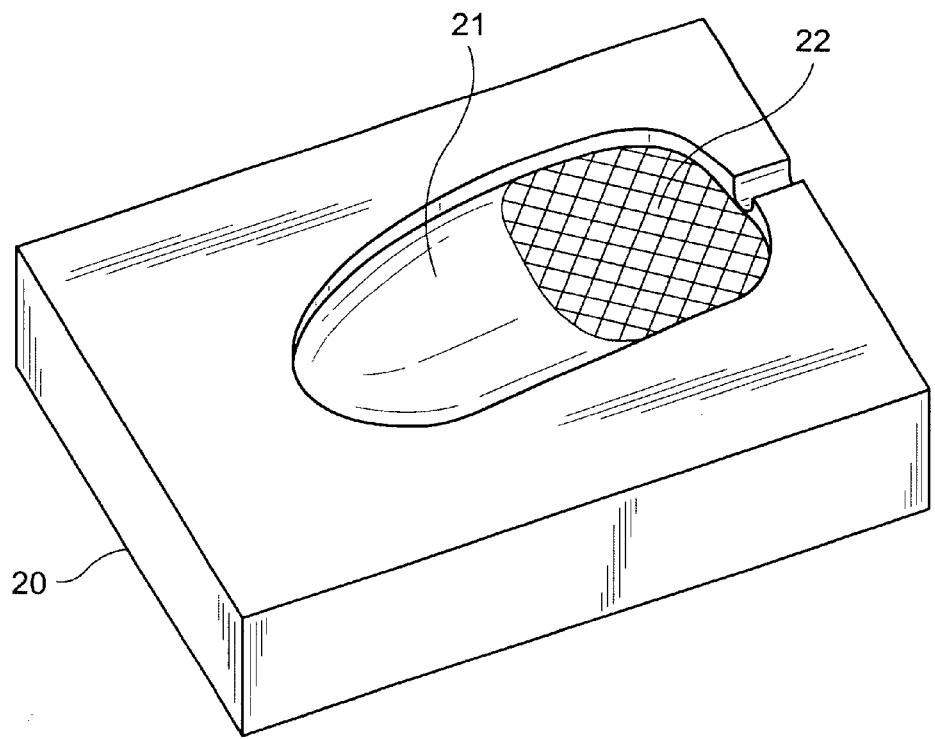
FIG. 4 is a top perspective view of a mold used to form the overlay of the resent invention.

Referring to FIG. 3, preferably, the bottom surface 14 at the first end 15 of the overlay 11 is formed with a textured or roughened surface 19 to enhance the adhesion of the emulsion to the overlay. The textured or roughened surface 19 may be provided during the molding process of the overlay or may be provided by an abrasive technique after forming of the overlay. FIG. 4 shows an injection mold 20 for forming the overlay 11. The mold 20 includes a cavity 21 in the shape, size and thickness of the overlay 11. The cavity 21 includes a textured or roughened surface 22 that is formed during the fabrication process of the mold by conventional cutting techniques such as hatching, milling, etching or grinding. Thus, during molding of the overlay 11, the textured surface 22 of the mold imparts a textured surface 19 on the bottom surface 14 of the overlay. Of course, as mentioned above, the textured surface 19 may be formed on the overlay 11 after molding by any variety of abrasive techniques such as etching, sanding, engraving or grinding. As a result of the textured surface 19, the peel strength of the adhesive layer 12 will be greater against the overlay 11 than against the natural nail of the wearer thereby preventing the adhesive layer from being stripped off the overlay when the overlay is removed from the natural nail. Therefore, the ornamental accessory 10 may be reused numerous times.

The adhesive layer 12 is made from an aqueous copolymer emulsion of acrylic ester and vinyl acetate. Such an emulsion is not hazardous to humans. Preferably, the emulsion comprises between 33–37% water and 63–67% copolymer and has a specific gravity of 1.07 and a viscosity of between 10,000–14,000 mPa-s. A suitable copolymer emulsion of this type is sold under the name POLYSOL PSA SE-6010 by Sumiko Tec Co. Ltd. of Tokohama, Japan and manufactured by Showa Highpolymer Co. Ltd. of Tokyo Japan. Decorative additives such as colored glitters or dyes may be added to the emulsion to enhance the overall cosmetic appeal of the accessory.

After forming the overlay 11, the aqueous copolymer emulsion is applied to the bottom surface 14 of the overlay at the first end 15 by brushing or spraying. The thickness to be applied is approximately 0.8 mm to 1.0 mm. Once the emulsion is applied to the overlay 11, it is heated in a heating tunnel at 30–40° C. for about 15 minutes. The emulsion is then allowed to dry in a clean environment at room temperature and constant humidity for about 72 hours whereby a substantial portion of water in the emulsion evaporates and the emulsion becomes transparent. This curing process can be accelerated by adding an additional heating step at 60–90° C. for about 15 minutes after the initial heating step. The subsequent drying time can then be reduced to approximately 5 hours. With both processes, the result is a tacky semi-solid pressure-sensitive adhesive layer 12 fixed to the bottom surface of the overlay 11. The adhesive layer 12 of the present invention has a shelf life of about 1–1½ years, however, should the layer begin to lose its adhesiveness, an aqueous solution can be reapplied to the layer to reactivate it.

Upon applying the tip, the first end 15 of the overlay 11 is placed on top of the wearer's fingernail and pressed in place. The top surface 13 of the overlay 11 may then be filed or buffed and clear nail polish may be applied. When the wearer wishes to remove the overlay, it is simply lifted off the natural nail. Since the bonding strength of the adhesive layer 12 is greater against the overlay 11 than it is against the natural nail, the adhesive layer stays with the overlay leaving no adhesive residue on the nail. Thus, the fingernail accessory of the present invention may be stored and reused when desired.

EXAMPLES

Tests of the adhesive layer 12 formed in accordance with the present invention reveal superior strength and durability. Table 1 summarizes the mechanical properties of the adhesive layer based on various tests. All tests were performed according to the testing methods according to JIS Z 0237. The peel strength test is performed by applying 23–27 g/m$^2$ of the emulsion on a test specimen, heating it at 110° for 60 seconds and allowing it to dry at room temperature for at least 24 hours. Test specimens of different materials (as shown in the table) are then stuck together at 20° C. and 65% relative humidity and tested after 20 minutes and 24 hours at a peel speed of 300 mm/min. Ball tack was measured at 20° C. and 65% relative humidity and holding power was measured 20 minutes after application at 20° C. and 65% relative humidity.

TABLE 1

| | | 50μ PET | | High Grade Paper (55 g/m$^2$) | |
|---|---|---|---|---|---|
| Time after sticking | | 20 min. | 24 hours | 20 min. | 24 hours |
| 180 degree Peel Strength (N/cm) | SUS 304 | 4.12 | 6.08 | 7.76 | Paper break 5.80 |
| | LDPE | 1.45 | 1.92 | 5.57 | |
| | PP | 2.63 (zipping) | | 6.57 | |
| | Glass | 3.29 | | 6.98 | |
| | ABS | 4.94 | | 7.57 | |
| | Hard PVC | 3.68 | | 7.72 | |
| Ball Tack (Ball No.) | | 5 | | 6 | |
| Holding Power (min.) | 20° C. | >1440 | | >1440 | |
| | 40° C. | >1440 | | >1400 | |

As can be seen from the above test results, the adhesive layer formed in accordance with the present invention provides significantly improved adhesiveness and superior strength, durability and holding power. The adhesiveness does not diminish even after prolonged use. Instead, the adhesiveness is maintained allowing for multiple reuses.

While there has been described what is presently believed to be the preferred embodiments of the invention, those skilled in the art will realize that various changes and modifications may be made to the invention without departing from the spirit of the invention, and it is intended to claim all such changes and modifications as fall within the scope of the invention.

What is claimed is:

1. An ornamental accessory for a fingernail comprising:
a reusable molded overlay having a top surface and a bottom surface and a first end and a second end, said first end having a shape and size approximating the shape and size of at least the end of a fingernail of a wearer for removable attachment thereto said bottom surface of said first end having an integrally molded textured surface formed thereon; and a reusable pressure-sensitive adhesive layer fixed to said textured bottom surface of said overlay at said first end and comprising a copolymer of acrylic ester and vinyl acetate, the bonding strength of said adhesive layer to said textured bottom surface being greater than the bonding strength of said adhesive layer to said fingernail thereby preventing said adhesive layer from being stripped from said textured bottom surface when said overlay is removed from said fingernail.

2. An ornamental accessory as defined in claim 1, wherein said copolymer is formed from an aqueous emulsion.

3. An ornamental accessory as defined in claim 2, wherein said aqueous emulsion comprises about 35% water and 65% copolymer.

4. An ornamental accessory as defined in claim 2, wherein said aqueous emulsion has a viscosity of between 10,000 and 14,000 mPa-s at 23° C.

5. An ornamental accessory as defined in claim 1, wherein said pressure-sensitive adhesive layer has a 180° peel strength of between 1.0 and 8.0 N/cm.

6. An ornamental accessory as defined in claim 1, wherein said overlay is made from a mixture of acrylonitrile-butadiene-styrene (ABS) plastic and a polycarbonate.

7. An ornamental accessory as defined in claim 1, wherein said first end of said overlay has a shape and size approximating the shape and size of the outer end of the fingernail of a wearer.

8. An ornamental accessory as defined in claim 1, wherein said first end of said overlay has a shape and size approximating the shape and size of a full fingernail of a wearer.

9. An ornamental accessory as defined in claim 1, wherein said pressure-sensitive adhesive layer includes a decorative additive.

10. An ornamental accessory as defined in claim 9, wherein said decorative additive is glitter.

11. An ornamental accessory as defined in claim 9, wherein said decorative additive is a dye.

12. A method for forming a pre-glued ornamental accessory for a fingernail comprising the steps of:
molding a reusable overlay having a top surface and a bottom surface and a first end and a second end, said first end having a shape and size approximating the shape and size of at least the end of a fingernail of a wearer for removable attachment thereto, and said bottom surface of said first end having a textured surface formed thereon during said molding;
applying an aqueous copolymer emulsion to said textured bottom surface of said overlay at said first end; and
allowing said aqueous copolymer emulsion to cure whereby a substantial portion of water in said emulsion is evaporated to form a reusable pressure-sensitive adhesive layer fixed to said overlay whereby the bonding strength of said adhesive layer to said textured bottom surface is greater than the bonding strength of said adhesive layer to said fingernail thereby preventing said adhesive layer from being stripped from said textured bottom surface when said overlay is removed from said fingernail.

13. A method for forming a pre-glued ornamental accessory for a fingernail as defined in claim 12, wherein said aqueous copolymer emulsion comprises a copolymer of acrylic ester and vinyl acetate.

14. A method for forming a pre-glued ornamental accessory for a fingernail as defined in claim 12, wherein said aqueous copolymer emulsion comprises about 35% water and 65% copolymer.

15. A method for forming a pre-glued ornamental accessory for a fingernail as defined in claim 12, wherein said aqueous copolymer emulsion has a viscosity of between 10,000 and 14,000 mPa-s at 23° C.

16. A method for forming a pre-glued ornamental accessory for a fingernail as defined in claim 12, wherein said dried aqueous copolymer emulsion has a 180° peel strength of between 1.0 and 8.0 N/cm.

17. A method for forming a pre-glued ornamental accessory for a fingernail as defined in claim 12, wherein said overlay is made from a mixture of acrylonitrile-butadiene-styrene (ABS) plastic and a polycarbonate.

18. A method for forming a pre-glued ornamental accessory for a fingernail as defined in claim 12, wherein said aqueous copolymer emulsion is applied to said over log brushing.

19. A method for forming a pre-glued ornamental accessory for a fingernail as defined in claim 12, wherein said aqueous copolymer emulsion is applied to said overlay by spraying.

20. A method for forming a pre-glued ornamental accessory for a fingernail as defined in claim 12, further comprising the step of reactivating said pressure-sensitive adhesive layer by adding an aqueous solution to said dried aqueous copolymer emulsion.

21. A method for forming a pre-glued ornamental accessory for a fingernail as defined in claim 12, wherein the step of allowing said aqueous copolymer emulsion to cure comprises the steps of:
heating the emulsion at a first temperature for a predetermined amount of time; and
allowing the emulsion to dry in a clean environment at room temperature.

22. A method for forming a pre-glued ornamental accessory for a fingernail as defined in claim 21, further comprising the step of heating the emulsion at a second temperature, which is higher than said first temperature, for a predetermined amount of time prior to allowing the emulsion to dry.

* * * * *